(12) United States Patent
Worthen et al.

(10) Patent No.: US 7,014,651 B2
(45) Date of Patent: *Mar. 21, 2006

(54) METHOD AND SYSTEM FOR TREATING CARDIAC ARREST USING HYPOTHERMIA

(75) Inventors: William J. Worthen, Coto de Caza, CA (US); Scott M. Evans, Santa Ana, CA (US); Suzanne C Winter, Coto de Caza, CA (US); David Balding, Mission Viejo, CA (US)

(73) Assignee: Alsius Corporation, Irvine, CA (US)

( * ) Notice: Subject to any disclaimer, the term of this patent is extended or adjusted under 35 U.S.C. 154(b) by 267 days.

This patent is subject to a terminal disclaimer.

(21) Appl. No.: 10/184,809

(22) Filed: Jun. 27, 2002

(65) Prior Publication Data

US 2002/0193853 A1 Dec. 19, 2002

Related U.S. Application Data

(63) Continuation of application No. 09/375,079, filed on Aug. 16, 1999, now Pat. No. 6,149,670, which is a continuation-in-part of application No. 09/266,452, filed on Mar. 11, 1999, now Pat. No. 6,458,150.

(51) Int. Cl.
*A61F 7/00* (2006.01)
(52) U.S. Cl. .................... 607/105; 128/898; 607/3
(58) Field of Classification Search .................. 607/96, 607/104–107, 113, 3, 5; 606/20–26; 604/27, 604/28; 128/898
See application file for complete search history.

(56) References Cited

U.S. PATENT DOCUMENTS

| | | | |
|---|---|---|---|
| 3,315,681 A | 4/1967 | Poppendiek | |
| 3,425,419 A | 2/1969 | Dato | 128/400 |
| 4,111,209 A | 9/1978 | Wolvek et al. | 128/400 |
| 4,305,388 A | 12/1981 | Brisson | |
| 4,416,280 A | 11/1983 | Carpenter et al. | |
| 4,416,281 A | 11/1983 | Cooper et al. | |
| 4,427,009 A | 1/1984 | Wells et al. | 128/400 |
| 4,512,163 A | 4/1985 | Wells et al. | 62/394 |
| 4,546,759 A | 10/1985 | Solar | |
| 4,686,085 A | 8/1987 | Osterholm | |
| 4,750,493 A | 6/1988 | Brader | 128/308 |
| 4,819,655 A | 4/1989 | Webler | |
| 4,840,617 A | 6/1989 | Osterholm | |
| 5,004,456 A | 4/1991 | Botterbusch et al. | |
| 5,139,496 A | 8/1992 | Hed | |
| 5,149,321 A | 9/1992 | Klatz et al. | |
| 5,234,405 A | 8/1993 | Klatz et al. | |
| 5,354,277 A | 10/1994 | Guzman et al. | |
| 5,385,540 A | 1/1995 | Abbott et al. | 604/4 |
| 5,395,314 A | 3/1995 | Klatz et al. | |
| 5,403,281 A | 4/1995 | O'Neill et al. | 604/113 |
| 5,474,533 A | 12/1995 | Ward et al. | 604/26 |

(Continued)

OTHER PUBLICATIONS

Safar, P. et al., "Improved Cerebral Resuscitation From Cardiac Arrest in Dogs with Mild Hypothermia Plus Blood Flow Promotion", Stroke, vol. 27, No. 1, Jan. 1996, pp. 105-113.*

(Continued)

*Primary Examiner*—Jeffrey R Jastrzab
(74) *Attorney, Agent, or Firm*—John L. Rogitz

(57) ABSTRACT

A method for treating cardiac arrest includes defibrillating the patient and/or ventilating the patient and/or administering a cardiac arrest drug such as epinephrine to resuscitate the patient, and then cooling the patient using one or more cooling catheter positioned in the central venous system of the patient.

8 Claims, 2 Drawing Sheets

U.S. PATENT DOCUMENTS

| | | | |
|---|---|---|---|
| 5,478,309 A | 12/1995 | Sweezer et al. | |
| 5,486,204 A | 1/1996 | Clifton | 607/96 |
| 5,486,208 A | 1/1996 | Ginsburg | 607/106 |
| 5,531,776 A | 7/1996 | Ward et al. | |
| RE35,352 E | 10/1996 | Peters | |
| 5,624,392 A * | 4/1997 | Saab | 604/113 |
| 5,695,457 A | 12/1997 | St. Goar et al. | 604/4 |
| 5,700,828 A | 12/1997 | Federowicz et al. | 514/419 |
| 5,716,386 A | 2/1998 | Ward et al. | |
| 5,755,756 A | 5/1998 | Freedman, Jr. et al. | 607/110 |
| 5,759,182 A | 6/1998 | Varney et al. | 606/21 |
| 5,800,375 A | 9/1998 | Sweezer et al. | |
| 5,837,003 A | 11/1998 | Ginsburg | 607/106 |
| 5,879,316 A | 3/1999 | Safar et al. | |
| 5,902,268 A | 5/1999 | Saab | 604/96 |
| 5,902,299 A | 5/1999 | Jayaraman | |
| 5,906,588 A | 5/1999 | Safar et al. | 604/64 |
| 5,975,081 A | 11/1999 | Hood et al. | 128/845 |
| 6,110,168 A | 8/2000 | Ginsburg | 606/27 |
| 6,126,684 A | 10/2000 | Gobin et al. | |
| 6,146,411 A | 11/2000 | Noda et al. | |
| 6,149,670 A | 11/2000 | Worthen et al. | |
| 6,149,673 A | 11/2000 | Ginsburg | 607/96 |
| 6,231,594 B1 | 5/2001 | Dae | |
| 6,264,679 B1 | 7/2001 | Keller et al. | 607/105 |
| 6,497,721 B1 | 12/2002 | Ginsburg et al. | 607/106 |
| 6,620,188 B1 * | 9/2003 | Ginsburg et al. | 607/106 |
| 6,726,710 B1 * | 4/2004 | Worthen et al. | 607/105 |
| 2001/0005791 A1 | 6/2001 | Ginsburg | 607/106 |
| 2001/0016764 A1 | 8/2001 | Dobak | 607/105 |
| 2001/0041923 A1 | 11/2001 | Dobak | 607/108 |
| 2002/0111616 A1 | 8/2002 | Dea et al. | 606/41 |
| 2003/0078641 A1 * | 4/2003 | Dobak, III | 607/105 |
| 2003/0195465 A1 * | 10/2003 | Worthen | 604/113 |

OTHER PUBLICATIONS

Gillinov et al., Superior Cerebral Protection With Profound Hypothermia During Circulatory Arrest, *Annals of Thoracic Surgery*, Jun. 1993, 55(6):1432-1439.

Ginsberg et al., Therapeutic Modulation of Brain Temperature: Relevance to Ischemic Brain Injury, *Cerebrovascular and Brain Metabolism Reviews*, 1992 Fall, 4(3):189-225.

Kay et al., Improving outcome from cardiac arrest in the hospital with a reorganized and strengthened chain of survival: an American view, *Resuscitation*, Jun 1996, 31(3): 181-186.

Onoe et al., The Effect of Pulsatile Perfusion on Cerebral Blood Flow During Profound Hypothermia with Total Circulatory Arrest, *Journal of Thoracic and Cardiovascular Surgery*, Jul 1994, 108(1):119-125.

Safar et al., Selective brain cooling after cardiac arrest, *Critical Care Medicine*, Jun 1996, 24(6):911-914.

Safar, P., Cerebral Resuscitation After Cardiac Arrest: Research Initiatives and Future Directions, *Annals of Emergency Medicine*, Feb, 1993 22(2 Pt 2):324-349.

Sessler, D., Deliberate Mild Hypothermia. *Journal of Neurosurgical Anesthesiology*, Jan. 1995, 7(1):38-46.

PUBLICATION: "Improving Outcome From Cardiac Arrest in the Hospital with a Reorganized and Strengthened Chain of Survival: An American View". Kaye et al. Resusitation vol. 31, pp. 181-186. Elsevier Science Ireland Ltd. 1996.

U.S. Appl. No. 09/133,813, Noda et al., Pending.
U.S. Appl. No. 09/266,452, Evans et al., Pending.
U.S. Appl. No. 09/282,971, Philips, Pending.
U.S. Appl. No. 09/321,350, Walker, Pending.
U.S. Appl. No. 09/390,600, Luo et al., Pending.
U.S. Appl. No. 09/413,752, Evans et al., Pending.
U.S. Appl. No. 09/413,753, Evans et al., Pending.
U.S. Appl. No. 09/456,110, Luo et al., Pending.
U.S. Appl. No. 09/477,490, Lasersohn et al., Pending.
U.S. Appl. No. 09/498,499, Worthen, Pending.
U.S. Appl. No. 09/540,693, Worthen et al., Pending.
U.S. Appl. No. 09/565,039, Worthen et al., Pending.

Paper: Future Directions for Resuscitation Research, 1997 (Tisherman et al.).

Paper: Hypothermic, Closed Circuit Pericardioperfusion: A Potential Cardioproective Technique in Acute Regional Ischemia, Jun. 1998 (Dave et al.).

* cited by examiner

Advanced life support algorithm for cardiac arrest using therapeutic hypothermia

Fig. 4  CPR

METHOD AND SYSTEM FOR TREATING CARDIAC ARREST USING HYPOTHERMIA

This application is a continuation of U.S. patent application Ser. No. 09/375,079, filed on Aug. 16, 1999, now U.S. Pat. No. 6,149,670, which is a continuation-in-part of 09/266,452, filed Mar. 11, 1999, now U.S. Pat. No. 6,458, 150.

RELATED APPLICATIONS

This application claims priority from U.S. patent application Ser. No. 09/565,039, filed May 3, 2000, now U.S. Pat. No. 6,432,124, which is a continuation of prior application Ser. No. 09/375,079, filed Aug. 18, 1999, now U.S. Pat. No. 6,149,670, which in turn claims priority from allowed U.S. patent application Ser. No. 09/266,452, filed Mar. 11, 1999. Priority is also claimed from allowed co-pending patent application Ser. No. 09/498,499, filed Feb. 4, 2000, which claims priority from patent application Ser. No. 09/305,613, filed May 5, 1999, now U.S. Pat. No. 6,368,304. Priority from all of the above documents is hereby claimed.

FIELD OF THE INVENTION

The present invention relates to methods and systems for treating cardiac arrest.

BACKGROUND

It has been discovered that the medical outcome for a patient suffering from severe brain trauma or from ischemia caused by stroke or heart attack is improved if the patient is cooled below normal body temperature (38° C.). As understood by the present invention, the medical outcome for many such patients might be significantly improved if the patients were to be moderately cooled to 32° C.–34° C. relatively quickly after an ischemic insult for a short period, e.g., 12–72 hours. It is believed that such cooling improves cardiac arrest patient outcomes by improving the mortality rate, in that many organs can benefit from the cooling, and by improving the neurological outcome for those patients that survive.

Systems and methods have been disclosed that propose cooling blood flowing to the brain through the carotid artery. An example of such systems and methods is disclosed in co-pending U.S. patent application Ser. No. 09/063,984, filed Apr. 21, 1998, owned by the present assignee and incorporated herein by reference. In the referenced application, various catheters are disclosed which can be advanced into a patient's carotid artery and through which coolant can be pumped in a closed circuit, to remove heat from the blood in the carotid artery and thereby cool the brain. The referenced devices have the advantage over other methods of cooling (e.g., wrapping patients in cold blankets) of being controllable, relatively easy to use, and of being capable of rapidly cooling and maintaining blood temperature at a desired set point.

As recognized in co-pending U.S. patent application Ser. No. 09/133,813, filed Aug. 13, 1998, owned by the present assignee and incorporated herein by reference, the above-mentioned advantages in treating ischemia by cooling can also be realized by cooling the patient's entire body, i.e., by inducing systemic hypothermia. The advantage of systemic hypothermia is that, as recognized by the present assignee, to induce systemic hypothermia a cooling catheter or other cooling device need not be advanced into the blood supply of the brain, but rather can be easily and quickly placed into the relatively large vena cava of the central venous system. Moreover, since many patients already are intubated with central venous catheters for other clinically approved purposes anyway, providing a central venous catheter that can also cool the blood requires no additional surgical procedures for those patients. A cooling central venous catheter is disclosed in the present assignee's co-pending U.S. patent application Ser. No. 09/253,109, filed Feb. 19, 1999 and Ser. No. 09/305,613, filed May 5, 1999, both of which are incorporated herein by reference.

The present invention understands that the above-mentioned benefits of hypothermia might be particularly suited for treating cardiac arrest. This is because outcomes for cardiac arrest patients currently are very poor, even when the patients can be resuscitated, since brain damage occurs as a result of the global ischemia caused by lack of blood flow before resuscitation. The severity of such brain damage, as understood herein, can potentially be alleviated by hypothermia.

SUMMARY OF THE INVENTION

A kit for lowering a patient's temperature includes a first catheter that has at least one fluid circulation passageway connectable to a source of coolant. In accordance with the present invention, the first catheter is configured for placement in a patient's vena cava via a groin entry point. Also, a second catheter has at least one fluid circulation passageway connectable to a source of coolant. As set forth below, the second catheter is configured for placement in a patient's circulatory system via a neck entry point.

In a preferred embodiment, the kit can include the source of coolant. Preferably, the source of coolant includes at least one thermal electric cooler (TEC) for heating or cooling coolant such that coolant is returned to the catheter to heat or cool the catheter. The kit can be incorporated in system that includes a ventilation system, and/or a defibrillator system, and/or a component containing a drug selected from the group consisting of: epinephrine, buffers, antiarrhythmics, and atropine.

In another aspect, a method for treating cardiac arrest in a patient includes defibrillating the patient, and lowering the patient's temperature using at least one catheter placed in the venous system of the patient.

In still another aspect, a method for treating cardiac arrest using hypothermia includes resuscitating the patient and inducing hypothermia in the patient.

In yet another aspect, a system for treating cardiac arrest in a patient includes at least one cooling catheter that is advanceable into the central venous system of the patient. The system further includes one or more of: a defibrillator, a ventilator, and a cardiac arrest drug delivery device engageable with the patient.

The details of the present invention, both as to its structure and operation, can best be understood in reference to the accompanying drawings, in which like reference numerals refer to like parts, and in which:

BRIEF DESCRIPTION OF THE DRAWINGS

FIG. 4 is a flow chart of the steps for cardiopulmonary resuscitation (CPR).

DETAILED DESCRIPTION OF THE PREFERRED EMBODIMENT

Figure 1:
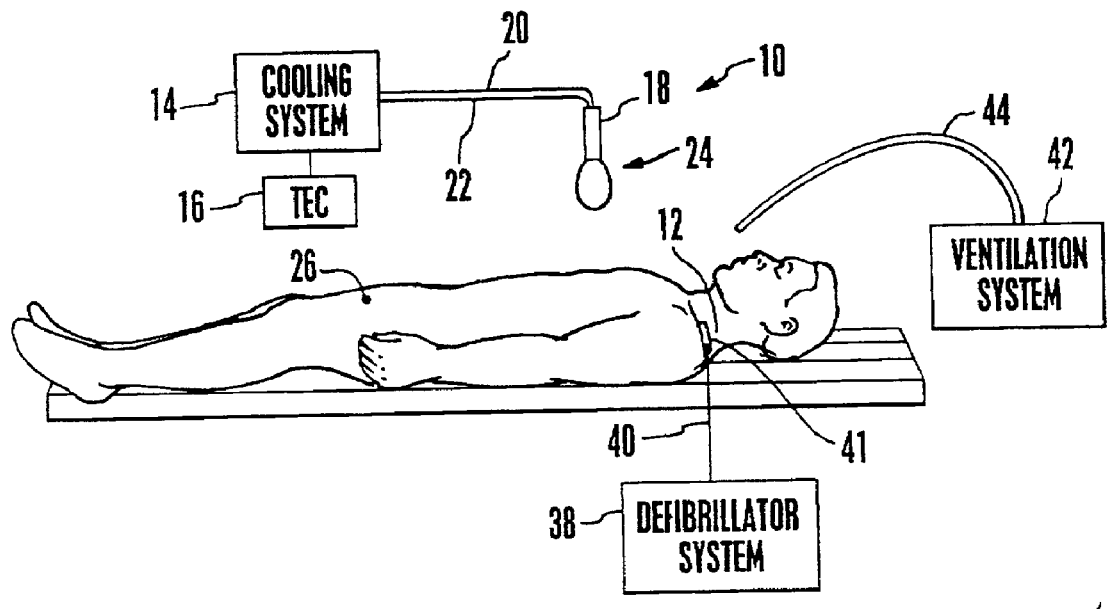
FIG. 1 is a schematic view of the cooling system using the first cooling catheter.

Referring initially to FIG. 1, a therapeutic system, generally designated 10, is shown for treating cardiac arrest in a patient 12. As shown, the system 10 includes a cooling system 14 that can be a water-bath system such as the system disclosed in the present assignee's co-pending U.S. patent application Ser. No. 09/220,897 filed Dec. 28, 1998 and incorporated herein by reference, or a cooling system including at least one thermal electric cooler (TEC) 16, as disclosed in the present assignee's co-pending U.S. patent application Ser. No. 09/260,950, filed Mar. 2, 1999 and incorporated herein by reference. In any case, the cooling system 14 can be considered a source of coolant, preferably sterile saline, for the catheters of the present invention.

As set forth in these applications, the cooling system 14 can include a heat exchanger, a pump, and, if desired, a controller. Preferably, the pump is a peristaltic pump, but other types of positive displacement pumps, such as but not limited to piston pumps and gear pumps, or even centrifugal pumps, can be used. A peristaltic pump is preferred in the present implementation because it can pump coolant without directly contacting the coolant, but instead simply by squeezing a tube through which the coolant flows. In this way, the pump is reusable, and only the present catheters and portions of the system 10 coming in direct contact with the coolant need be made disposable to render an advantageously disposable and sterile coolant delivery system. The controller controls the rate at which coolant is pumped by the pump and, if desired, the rate at which heat is added or subtracted from the coolant. The controller can be implemented by a software-executing processor or by discrete logic circuits or other electronic circuitry device to establish a desired patient temperature by appropriately controlling the pump and/or heat exchanger in response to a temperature signal derived from a sensor in the patient 12.

As shown in FIG. 1, a first cooling catheter 18 can communicate with the cooling system 14 via coolant supply and return lines 20, 22. The coolant lines 20, 22 can be IV lines or tubes or other suitable fluid conduits, such as metal (steel) tubes. When the coolant lines 20, 22 are plastic tubes, they can be connected to the catheter 18 and the cooling system 14 by suitable connecting structure, such as Luer fittings, interference fits, solvent bonding, heat staking, ultrasonic welding, and the like.

The first cooling catheter 18 includes a heat exchange region 24. The heat exchange region 24 can be established by one or more hollow fibers, as disclosed in the above-referenced U.S. patent application Ser. No. 09/133,813. Alternatively, the heat exchange region 24 can include one or more cooling membranes such as balloons as disclosed in the above-referenced U.S. patent application Ser. Nos. 09/253,109 and 09/305,613. For example, the heat exchange region 24 of the first catheter 18 can be established by four axially staggered balloons, each ten millimeters in diameter when inflated with coolant.

In any case, as set forth in the referenced applications, coolant is circulated in a closed fluid communication loop between the heat exchange region 24 and cooling system 14 to remove heat from the patient 12. As set forth in greater detail below, the first catheter 18 is advanced (preferably through an introducer sheath) into the vena cava of the patient 12 through a groin entry point 26 to establish hypothermia in the patient 12. Preferably, the catheter 18 is advanced either through the saphenous vein or femoral vein in accordance with the method described below.

Figure 2:
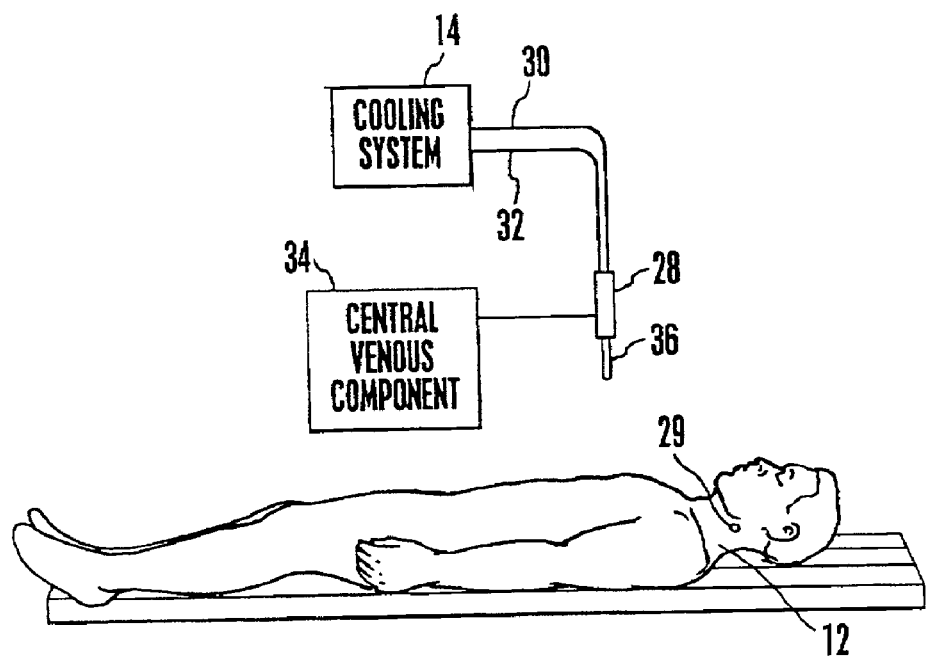
FIG. 2 is a schematic view of the cooling system using the second cooling catheter.

In addition to or in lieu of the first catheter 18, a second cooling catheter 28 (FIG. 2) which is configured for use as a central venous catheter can be advanced into the central venous system of the patient through a neck entry point 29. The second catheter 28 can be embodied by the catheter disclosed in the above-referenced patent application Ser. Nos. 09/253,109 and 09/305,613. Accordingly, the second catheter 28 can communicate with the cooling system 14 via coolant supply and return lines 30, 32. Also, the second catheter 28 can communicate with one or more central venous components 34, such as IV infusion devices, drug delivery syringes for infusing epinephrine, blood withdrawal devices, and so on.

As disclosed in the referenced applications, the second catheter 28 includes a heat exchange region 36 that can be established by one or more membranes such as balloons, although it could be established by hollow fibers in the manner of the catheter 18, but on a smaller scale. The catheter 28 can be advanced into the superior vena cava through the jugular vein or subclavian vein to cool the patient 12 by means of coolant circulating in a closed loop between the cooling system 14 and the balloon 36. As mentioned above, the second catheter 28 can also be used to undertake conventional central venous catheter functions.

Referring back to FIG. 1, in addition to the cooling components discussed above, the system 10 can include a heart defibrillator system 38 that can be engaged with the patient 12 by means of one or more defibrillator connecting lines 40 with associated engaging paddles/electrodes 41. Moreover, the system 10 can include a ventilation system 42 that ventilates the patient 12 by means of an endotracheal tube 44 or other equivalent device such as a ventilating mask.

Figure 3:
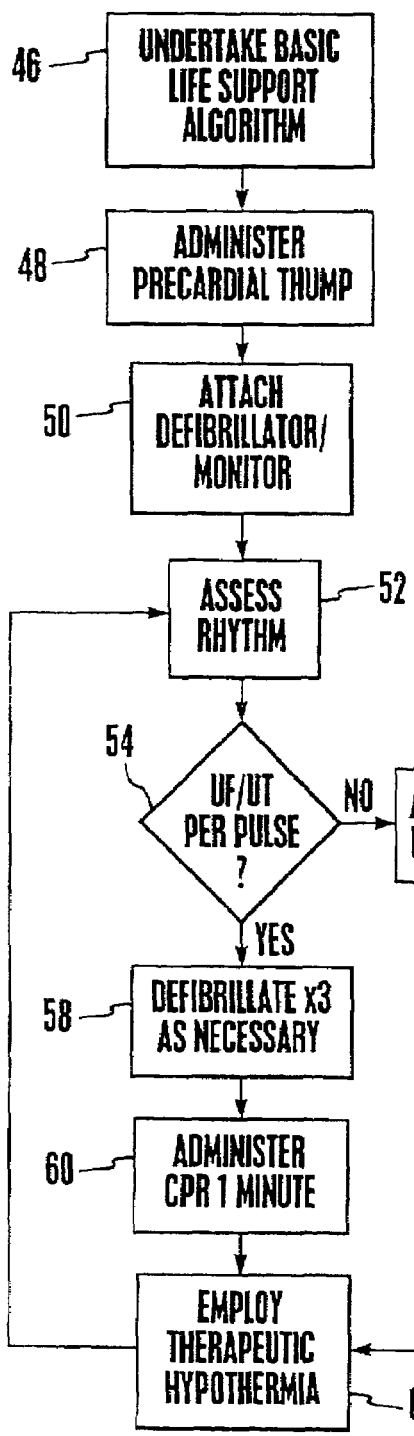
FIG. 3 is a flow chart of the present invention for treating cardiac arrest in a patient.
Figure 3:
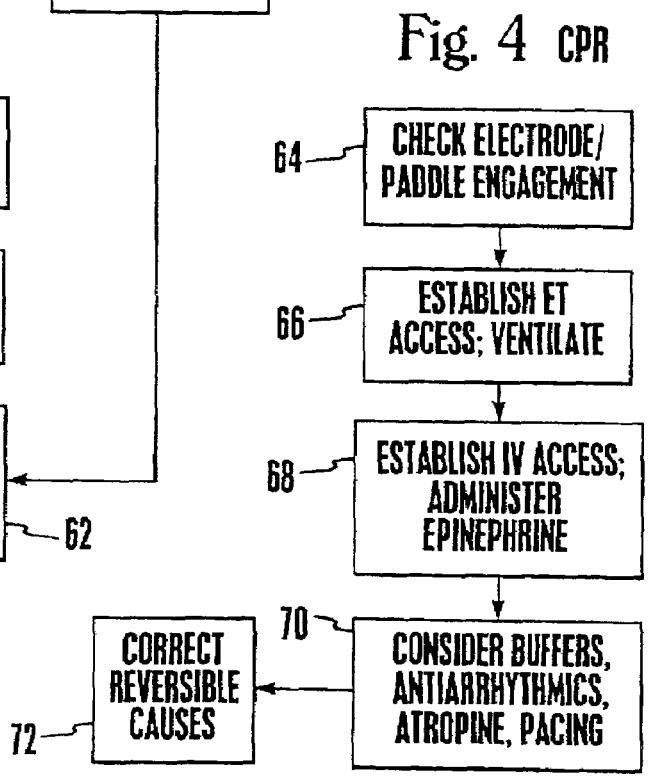

The process of the present invention can be appreciated in reference to FIG. 3. Commencing at block 46, basic life support algorithms are undertaken on a patient suffering from cardiac arrest. The basic life support activities can include one or more of the cardiopulmonary resuscitation (CPR) acts discussed below in reference to FIG. 4.

At block 48, in an attempt to quickly start the patient's heart beating again, particularly in the absence of a defibrillator, a precordial thump can be administered to the patient's chest. In addition, or if and when the defibrillator system 38 becomes available, at block 50 the defibrillator is engaged with the patient and the patient is defibrillated to start the patient's heart beating.

After initial defibrillation, the patient's heart rhythm is assessed at block 52. At decision diamond 54 it is determined in accordance with cardiac arrest resuscitation standards whether the patient exhibits ventricular fibrillation (VF) or ventricular tachycardia (VT). VF is defined as a pulseless, chaotic, disorganized rhythm characterized by an undulating irregular pattern that varies in size and shape with a ventricular waveform greater than 150 beats per minute. If no VF/VT is detected, indicating that the patient's heart is beating normally, some or all of the CPR acts shown in FIG. 4 are administered as necessary at block 56 for, e.g., up to three minutes.

If, on the other hand, it is determined at decision diamond 56 that the patient exhibits VF/VT, the patient is defibrillated up to, e.g., three times at block 58. In one preferred embodiment, defibrillation energy levels are 200 J (2 J/kg) for the first shock, 200J–300 J (2–4 J/kg) for the second shock, and 360 J (4 J/kg) for the third and subsequent shocks (weight-based dosages are pediatric recommendations). CPR is then administered at block 60 for up to, e.g., one minute.

In accordance with the present invention, after defibrillation and CPR, moderate hypothermia is induced in the patient at block 62 to alleviate the results of global ischemia arising from cardiac arrest. It is to be understood that the step shown at block 62 can be undertaken at other convenient times including before defibrillation and CPR or concurrently therewith. In any case, the patient's temperature is lowered below normal body temperature, and as low as 32° C., by advancing one or both of the catheters 18, 28 into the patient 12 and then circulating coolant through the catheter 18, 28.

In one embodiment of the present method, the first catheter 18 is initially advanced into the vena cava through the groin to cool the patient while resuscitation personnel require access to the neck for intubation and for establishing rapid IV access. When CPR is complete, the second catheter 28 can be advanced into the vena cava through the relatively less septic neck, and if desired the first catheter 18 can be removed from the relatively more septic groin area. It is to be understood that while this is one preferred sequence of the order of steps for inducing hypothermia in a cardiac arrest patient, other sequences can be used. For example, the first catheter 18 can be used exclusively to the second catheter 28, the second catheter 28 can be used exclusively to the first catheter 18, or both catheters 18, 28 can be used together simultaneously.

FIG. 4 shows that CPR can include but need not be limited to checking defibrillator electrode/paddle engagement on the patient at block 64. Also, CPR can include establishing endotracheal access with the ET tube 44 at block 66 and then ventilating the patient using the ventilation system 42. If tracheal intubation is not possible, a laryngeal mask airway or Combitube can be used as alternatives.

Moreover, at block 68 intravenous (IV) access can be established using one of the catheters 18, 28 or another catheter such as a Swan-Ganz catheter, and then cardiac arrest drugs such as epinephrine can be administered. If IV access is not attainable, epinephrine can be administered via the ET tube 44 using at least twice the intravascular dosage of at least 1 mg (0.01 mg/kg) every 3 minutes.

At block 70 other drugs can be considered for administration including buffers, antiarrythmics, and atropine, and the installation of a pacemaker can also be undertaken. Any causes that can be corrected (such as, e.g., blocked airways) are corrected at block 72.

While the particular METHOD AND APPARATUS FOR ESTABLISHING AND MAINTAINING THERAPEUTIC HYPOTHERMIA as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. ?112, sixth paragraph, unless the element is expressly recited using the phrase "means for".

What is claimed is:

1. A method for responding to symptoms of a heart malady in a patient, comprising:
   responding to a heart attack in a patient by inducing hypothermia in the patient using at least one catheter placed in any blood vessel of the patient by circulating heat exchange fluid through the catheter while the catheter is positioned in the patient's circulatory system, such that the heat exchange fluid does not enter the patient's bloodstream.

2. The method of claim 1, comprising inducing moderate hypothermia.

3. The method of claim 1, comprising inducing mild hypothermia.

4. The method of claim 1, wherein the blood vessel is the vena cava, and the catheter is not advanced to the heart.

5. The method of claim 1, comprising advancing the catheter through a groin entry point.

6. The method of claim 1, comprising advancing the catheter through an upper body entry point affording access to the jugular vein, the catheter being advanced through the jugular vein to the superior vena cava, the catheter being positioned in the superior vena cava to cool blood therein during the act of inducing.

7. The method of claim 1, comprising advancing the catheter through an upper body entry point affording access to the subclavian vein, the catheter being advanced through the subclavian vein to the superior vena cava, the catheter being positioned in the superior vena cava to cool blood therein during the act of inducing.

8. A method comprising:
   treating cardiac arrest in a patient by inducing hypothermia in the patient using at least one catheter placed in any blood vessel of the patient by circulating heat exchange fluid through the catheter while the catheter is positioned in the patient's circulatory system, such that the heat exchange fluid does not enter the patient's bloodstream.

* * * * *